United States Patent
Hendricks et al.

(10) Patent No.: US 9,784,263 B2
(45) Date of Patent: Oct. 10, 2017

(54) HEAT EXCHANGE SYSTEM FOR PATIENT TEMPERATURE CONTROL WITH EASY LOADING HIGH PERFORMANCE PERISTALTIC PUMP

(71) Applicant: Zoll Circulation, Inc., San Jose, CA (US)

(72) Inventors: Austin Reid Hendricks, Union City, CA (US); Christo Petrov Pamichev, Cupertino, CA (US); Venkata Vishnu Gurukula, Mountain View, CA (US); Jeremy Thomas Dabrowiak, Redwood City, CA (US)

(73) Assignee: ZOLL CIRCULATION, INC., San Jose, CA (US)

( * ) Notice: Subject to any disclaimer, the term of this patent is extended or adjusted under 35 U.S.C. 154(b) by 101 days.

(21) Appl. No.: 14/534,718

(22) Filed: Nov. 6, 2014

(65) Prior Publication Data
US 2016/0131127 A1    May 12, 2016

(51) Int. Cl.
*F04B 43/12* (2006.01)
*A61M 5/142* (2006.01)
*A61F 7/00* (2006.01)

(52) U.S. Cl.
CPC ...... *F04B 43/1223* (2013.01); *F04B 43/1276* (2013.01); *F04B 43/1284* (2013.01); *A61F 2007/0054* (2013.01); *A61M 5/14232* (2013.01)

(58) Field of Classification Search
CPC .............. F04B 43/1253; F04B 43/1276; F04B 43/1284; A61M 5/14232

(Continued)

(56) References Cited

U.S. PATENT DOCUMENTS 1,459,112 A    6/1923   Mehl
1,726,761 A    9/1929   Palmer
(Continued)

FOREIGN PATENT DOCUMENTS

DE    19531935       2/1997
EP    0663529 B1     5/1997
(Continued)

OTHER PUBLICATIONS

F.W. Behmann, E. Bontke, "Die Regelung der Wärmebildung bei künstlicher Hypothermie", PFFügers Archiv, Bd. 266, S. 408-421 (1958).

(Continued)

*Primary Examiner* — Peter J Bertheaud
(74) *Attorney, Agent, or Firm* — John L. Rogitz (57) ABSTRACT

A peristaltic pump has an arcuate raceway with a partially concave inner surface extending through an arc of at least one hundred eighty degrees (180°). The arc defines a midpoint, and a rotor faces the inner surface of the raceway and is both rotatable relative to the raceway and translationally movable relative to the raceway between a pump position, wherein the rotor is spaced from the midpoint a first distance, and a tube load position, wherein the rotor is spaced from the midpoint a second distance greater than the first distance. A motor is coupled to the rotor to rotate the rotor plural are rollers arranged on the rotor to contact tubing disposed between the rotor and the raceway when the rotor is in the pump position. The motor is prevented from stopping at a predetermined angular position to facilitate loading and unloading tubing.

8 Claims, 7 Drawing Sheets

(58) Field of Classification Search
USPC .............................. 417/477.3, 477.8, 477.11
See application file for complete search history.

(56) References Cited

U.S. PATENT DOCUMENTS

| | | | |
|---|---|---|---|
| 1,857,031 A | 5/1932 | Schaffer | |
| 2,663,030 A | 12/1953 | Dahlberg | |
| 2,673,987 A | 4/1954 | Upshaw et al. | |
| 2,987,004 A * | 6/1961 | Murray ..................... | F01C 5/08 |
| | | | 417/475 |
| 3,140,716 A | 7/1964 | Harrison et al. | |
| 3,225,191 A | 12/1965 | Calhoun | |
| 3,369,549 A | 2/1968 | Armao | |
| 3,425,419 A | 2/1969 | Actis Dato | |
| 3,504,674 A | 4/1970 | Swenson | |
| 3,726,269 A | 4/1973 | Webster, Jr. | |
| 3,744,555 A | 7/1973 | Fletcher et al. | |
| 3,751,077 A | 8/1973 | Hiszpanski | |
| 3,937,224 A | 2/1976 | Uecker | |
| 3,945,063 A | 3/1976 | Matsuura | |
| 4,038,519 A | 7/1977 | Foucras | |
| 4,065,264 A | 12/1977 | Lewin | |
| 4,103,511 A | 8/1978 | Kress et al. | |
| 4,126,132 A | 11/1978 | Portner et al. | |
| 4,153,048 A | 5/1979 | Magrini | |
| 4,173,228 A | 11/1979 | Van Steenwyk et al. | |
| 4,181,132 A | 1/1980 | Parks | |
| 4,181,245 A | 1/1980 | Garrett et al. | |
| 4,298,006 A | 11/1981 | Parks | |
| 4,459,468 A | 7/1984 | Bailey | |
| 4,532,414 A | 7/1985 | Shah et al. | |
| 4,552,516 A * | 11/1985 | Stanley ............... | F04B 43/1253 |
| | | | 24/517 |
| 4,554,793 A | 11/1985 | Harding, Jr. | |
| 4,581,017 A | 4/1986 | Sahota | |
| 4,638,436 A | 1/1987 | Badger et al. | |
| 4,653,987 A | 3/1987 | Tsuji et al. | |
| 4,661,094 A | 4/1987 | Simpson | |
| 4,665,391 A | 5/1987 | Spani | |
| 4,672,962 A | 6/1987 | Hershenson | |
| 4,754,752 A | 7/1988 | Ginsburg et al. | |
| 4,787,388 A | 11/1988 | Hofmann | |
| 4,813,855 A | 3/1989 | Leveen et al. | |
| 4,849,196 A | 7/1989 | Yamada et al. | |
| 4,852,567 A | 8/1989 | Sinofsky | |
| 4,860,744 A | 8/1989 | Johnson et al. | |
| 4,906,237 A | 3/1990 | Johansson et al. | |
| 4,925,376 A * | 5/1990 | Kahler ................ | F04B 43/1284 |
| | | | 417/477.11 |
| 4,941,475 A | 7/1990 | Williams et al. | |
| 5,080,089 A | 1/1992 | Mason et al. | |
| 5,092,841 A | 3/1992 | Spears | |
| 5,103,360 A | 4/1992 | Maeda | |
| 5,106,360 A | 4/1992 | Ishiwara et al. | |
| 5,174,285 A | 12/1992 | Fontenot | |
| 5,192,274 A | 3/1993 | Bierman | |
| 5,195,965 A | 3/1993 | Shantha | |
| 5,211,631 A | 5/1993 | Sheaff | |
| 5,263,925 A | 11/1993 | Gilmore et al. | |
| 5,269,758 A | 12/1993 | Taheri | |
| 5,281,215 A | 1/1994 | Milder | |
| 5,304,214 A | 4/1994 | DeFord et al. | |
| 5,342,301 A | 8/1994 | Saab | |
| 5,344,436 A | 9/1994 | Fontenot et al. | |
| 5,370,675 A | 12/1994 | Edwards et al. | |
| 5,383,856 A | 1/1995 | Bersin | |
| 5,403,281 A | 4/1995 | O'Neill et al. | |
| 5,433,740 A | 7/1995 | Yamaguchi | |
| 5,437,673 A | 8/1995 | Baust et al. | |
| 5,458,639 A | 10/1995 | Tsukashima et al. | |
| 5,486,207 A | 1/1996 | Mahawili | |
| 5,486,208 A | 1/1996 | Ginsburg | |
| 5,507,792 A | 4/1996 | Mason et al. | |
| 5,531,714 A | 7/1996 | Dahn et al. | |
| 5,531,776 A | 7/1996 | Ward et al. | |
| 5,624,392 A | 4/1997 | Saab | |
| 5,634,907 A | 6/1997 | Rani et al. | |
| 5,676,670 A | 10/1997 | Kim | |
| 5,701,905 A | 12/1997 | Esch | |
| 5,706,889 A | 1/1998 | Bach et al. | |
| 5,709,564 A | 1/1998 | Yamada et al. | |
| 5,709,654 A | 1/1998 | Klatz et al. | |
| 5,716,386 A | 2/1998 | Ward et al. | |
| 5,730,720 A | 3/1998 | Sites et al. | |
| 5,733,319 A | 3/1998 | Neilson et al. | |
| 5,737,782 A | 4/1998 | Matsuura et al. | |
| 5,759,017 A | 6/1998 | Patton et al. | |
| 5,776,079 A | 7/1998 | Cope et al. | |
| 5,788,647 A | 8/1998 | Eggers | |
| 5,837,003 A | 11/1998 | Ginsburg | |
| 5,862,675 A | 1/1999 | Scaringe et al. | |
| 5,895,418 A | 4/1999 | Saringer | |
| 5,908,407 A | 6/1999 | Frazee et al. | |
| 5,957,963 A | 9/1999 | Dobak, III | |
| 5,980,561 A | 11/1999 | Kolen et al. | |
| 6,019,783 A | 2/2000 | Philips et al. | |
| 6,042,559 A | 3/2000 | Dobak, III | |
| 6,051,019 A | 4/2000 | Dobak, III | |
| 6,059,825 A | 5/2000 | Hobbs et al. | |
| 6,096,068 A | 8/2000 | Dobak, III et al. | |
| 6,110,139 A | 8/2000 | Loubser | |
| 6,117,065 A | 9/2000 | Hastings et al. | |
| 6,117,105 A | 9/2000 | Bresnaham et al. | |
| 6,124,452 A | 9/2000 | Di Magno | |
| 6,126,684 A | 10/2000 | Gobin et al. | |
| 6,146,141 A | 11/2000 | Schumann | |
| 6,146,411 A | 11/2000 | Noda et al. | |
| 6,148,634 A | 11/2000 | Sherwood | |
| 6,149,670 A | 11/2000 | Worthen et al. | |
| 6,149,677 A | 11/2000 | Dobak, III | |
| 6,149,806 A | 11/2000 | Baer | |
| 6,231,594 B1 | 5/2001 | Dae | |
| 6,283,940 B1 | 9/2001 | Mulholland | |
| 6,299,599 B1 | 10/2001 | Pham et al. | |
| 6,338,727 B1 | 1/2002 | Noda et al. | |
| 6,383,144 B1 | 5/2002 | Mooney et al. | |
| 6,409,747 B1 | 6/2002 | Gobin et al. | |
| 6,416,533 B1 | 7/2002 | Gobin et al. | |
| 6,428,563 B1 | 8/2002 | Keller | |
| 6,450,990 B1 | 9/2002 | Walker et al. | |
| 6,464,666 B1 | 10/2002 | Augustine et al. | |
| 6,464,716 B1 | 10/2002 | Dobak, III et al. | |
| 6,527,798 B2 | 3/2003 | Ginsburg et al. | |
| 6,530,946 B1 | 3/2003 | Noda et al. | |
| 6,544,282 B1 | 4/2003 | Dae et al. | |
| 6,551,309 B1 | 4/2003 | Le Pivert | |
| 6,554,791 B1 | 4/2003 | Cartledge et al. | |
| 6,605,106 B2 | 8/2003 | Schwartz | |
| 6,610,083 B2 | 8/2003 | Keller et al. | |
| 6,620,187 B2 | 9/2003 | Carson et al. | |
| 6,620,188 B1 | 9/2003 | Ginsburg et al. | |
| 6,624,679 B2 | 9/2003 | Tomaivolo et al. | |
| 6,635,076 B1 | 10/2003 | Ginsburg | |
| 6,673,098 B1 | 1/2004 | Machold et al. | |
| 6,679,906 B2 | 1/2004 | Hammack et al. | |
| 6,685,731 B2 | 2/2004 | Kushnir et al. | |
| 6,685,733 B1 | 2/2004 | Dae et al. | |
| 6,695,874 B2 | 2/2004 | Machold et al. | |
| 6,706,060 B2 | 3/2004 | Tzeng et al. | |
| 6,716,188 B2 | 4/2004 | Noda et al. | |
| 6,719,723 B2 | 4/2004 | Werneth | |
| 6,719,779 B2 | 4/2004 | Daoud | |
| 6,726,653 B2 | 4/2004 | Noda et al. | |
| 6,740,109 B2 | 5/2004 | Dobak, III | |
| 6,743,201 B1 | 6/2004 | Donig et al. | |
| 6,799,342 B1 | 10/2004 | Jarmon | |
| 6,843,800 B1 | 1/2005 | Dobak, III | |
| 6,878,156 B1 | 4/2005 | Noda | |
| 6,887,263 B2 | 5/2005 | Bleam et al. | |
| 6,893,419 B2 | 5/2005 | Noda et al. | |
| 6,969,399 B2 | 11/2005 | Schock et al. | |
| 7,070,612 B1 | 7/2006 | Collins et al. | |
| 7,104,769 B2 * | 9/2006 | Davis ................... | B41J 2/17596 |
| | | | 417/477.9 |

(56) References Cited

U.S. PATENT DOCUMENTS

| | | | |
|---|---|---|---|
| 7,140,850 B2* | 11/2006 | Otis, Jr. | F04B 43/1253 417/477.1 |
| 7,510,569 B2 | 3/2009 | Dae et al. | |
| 7,666,215 B2 | 2/2010 | Callister et al. | |
| 7,713,036 B2* | 5/2010 | Kojima | F04B 43/1253 417/477.3 |
| 7,822,485 B2 | 10/2010 | Collins | |
| 7,846,193 B2 | 12/2010 | Dae et al. | |
| 7,857,781 B2 | 12/2010 | Noda et al. | |
| 7,892,269 B2 | 2/2011 | Collins et al. | |
| 8,105,262 B2 | 1/2012 | Noda et al. | |
| 8,105,263 B2 | 1/2012 | Noda et al. | |
| 8,105,264 B2 | 1/2012 | Noda et al. | |
| 8,109,894 B2 | 2/2012 | Noda et al. | |
| 8,128,384 B2* | 3/2012 | Mou | F04B 43/1284 417/477.11 |
| 8,226,605 B2 | 7/2012 | Faries, Jr. et al. | |
| 8,272,857 B2 | 9/2012 | Norman et al. | |
| 2001/0031946 A1 | 10/2001 | Walker et al. | |
| 2001/0047196 A1 | 11/2001 | Ginsburg et al. | |
| 2002/0013569 A1 | 1/2002 | Sterman et al. | |
| 2002/0022823 A1 | 2/2002 | Luo et al. | |
| 2002/0145525 A1 | 10/2002 | Friedman et al. | |
| 2002/0183692 A1 | 12/2002 | Callister | |
| 2002/0198579 A1 | 12/2002 | Khanna | |
| 2003/0236496 A1 | 12/2003 | Samson et al. | |
| 2004/0026068 A1 | 2/2004 | Schmidt et al. | |
| 2004/0089058 A1 | 5/2004 | De Haan et al. | |
| 2004/0102825 A1 | 5/2004 | Daoud | |
| 2004/0104018 A1 | 6/2004 | Hughes et al. | |
| 2004/0143311 A1 | 7/2004 | Machold et al. | |
| 2004/0210231 A1 | 10/2004 | Boucher et al. | |
| 2005/0156744 A1 | 7/2005 | Pires | |
| 2006/0064146 A1 | 3/2006 | Collins | |
| 2006/0069418 A1 | 3/2006 | Schock et al. | |
| 2006/0122673 A1 | 6/2006 | Callister et al. | |
| 2006/0210424 A1 | 9/2006 | Mallett et al. | |
| 2006/0293734 A1 | 12/2006 | Scott et al. | |
| 2007/0007640 A1 | 1/2007 | Harnden et al. | |
| 2007/0076401 A1 | 4/2007 | Carrez et al. | |
| 2008/0230530 A1 | 9/2008 | Augustine et al. | |
| 2008/0262409 A1 | 10/2008 | Derrico et al. | |
| 2008/0267599 A1 | 10/2008 | Arnold et al. | |
| 2009/0247963 A1 | 10/2009 | Bleam et al. | |
| 2009/0299287 A1 | 12/2009 | Carson et al. | |
| 2010/0129248 A1 | 5/2010 | Mou | |
| 2011/0022136 A1 | 1/2011 | Scott et al. | |
| 2011/0046551 A1 | 2/2011 | Augustine et al. | |
| 2011/0137249 A1 | 6/2011 | Collins et al. | |
| 2011/0184253 A1 | 7/2011 | Archer et al. | |
| 2011/0208278 A1 | 8/2011 | Machold et al. | |
| 2011/0213305 A1 | 9/2011 | Jönsson et al. | |
| 2012/0158103 A1 | 6/2012 | Bledsoe | |
| 2013/0331774 A1 | 12/2013 | Farrell et al. | |
| 2014/0081202 A1 | 3/2014 | Tsoukalis | |

FOREIGN PATENT DOCUMENTS

| | | |
|---|---|---|
| GB | 2040169 | 8/1980 |
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| WO | 9001682 | 2/1990 |
| WO | 9304727 | 3/1993 |
| WO | 9400177 | 1/1994 |
| WO | 9401177 | 1/1994 |
| WO | 95-03680 | 2/1995 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0126719 | 4/2001 |
| WO | 0164146 | 9/2001 |
| WO | 0176517 | 10/2001 |
| WO | 0183001 | 11/2001 |
| WO | 2012-175089 | 12/2012 |
| WO | 2014160422 A1 | 10/2014 |
| WO | 2015122938 A1 | 8/2015 |

OTHER PUBLICATIONS

F.W. Behmann, E. Bontke, "Intravasale Kühlung", Pflügers Archiv, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman: "Hypothermic Coagulopathy in trauma: Effect of Varying levels of Hypothermia on Enzyme Speed Function, Platelet Function, and Fibrinolytic Activity". The Journal of Trauma: Injury, Infection, and Critical Care, Vo. 44, No. 5 (1998).

Jeremy Thomas Dabrowiak, Christoph Matthias Pistor, Craig Wendell Pendry, Christo Petrov Pamichev, "Fluid Cassette with Tensioned Polymeric Membranes for Patient Heat Exchange System" related pending U.S. Appl. No. 14/180,613, non-final office action dated May 19, 2016.

Christoph Matthias Pistor, Jeremy Thomas Dabrowiak, Craig Wendell Pendry, Christo Petroc Pamichev, "Fluid Cassette with Polymeric Membranes and Integral Intel and Outlet Tubes for Patient Heat Exchange System", related pending U.S. Appl. No. 14/180,655, non-final office action dated May 18, 2016.

Jeremy Thomas Dabrowiak, Eric Peterson, "Patient Heat Exchange System with Transparent Wall for Viewing Circulating Refrigerant", related pending U.S. Appl. No. 141276,202, non-final office action dated May 19, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613, applicant's response to non-final office action filed Jun. 1, 2016.

Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.

Jeremy Thomas Dabrowiak, Eric Peterson, "Patient Heat Exchange System with Transparent Wall for Viewing Circulating Refrigerant", related pending U.S. Appl. No. 14/276,202, applicant's response to non-final office action filed Jun. 1, 2016.

Jeremy Thomas Dabrowiak, Mark Davey, "Serpentine Heat Exchange Assembly for Removable Engagement with Patient Heat Exchange System", file history of related U.S. Appl. No. 14/675,421, filed Mar. 31, 2015.

James Mazzone, "Proximal Mounting of Temperature Sensor in INtravascular Temperature Management Catheter", file history of related U.S. Appl. No. 14/675,452, filed Mar. 31, 2015.

Jeremy Thomas Dabrowiak, Craig Wendell Pendry, Christoph Matthias Pistor, "Cold Plate Design in Heat Exchanger for Intravascular Temperature Management Catheter and/or Heat Exchange Pad", file history for related U.S. Appl. No. 14/675,504, filed Mar. 31, 2015.

Christo Petrov Pamichev, Jeremy Thomas Dabrowiak, "Working Fluid Cassette with Hinged Plenum or Enclosure for Interfacing Heat Exchanger with Intravascular Temperature Management Catheter", filed history of related U.S. Appl. No. 14/676,672, filed Apr. 1, 2015.

Christo Petrov Pamichev, Jeremy Thomas Dabrowiak, "Heat Exchange System for Patient Temperature Control with Easy Loading High Performance Peristaltic Pump", file history of related U.S. Appl. No. 14/676,682, filed Apr. 1, 2015.

(56) References Cited

OTHER PUBLICATIONS

Jeremy Thomas Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016.

Jeremy Thomas Dabrowiak, "Heat Exchange System for Patient Temperature Control with Multiple Coolant Chambers for Multiple Heat Exchange Modalities", related pending U.S. Appl. No. 14/175,545 applicants response to non-final office action filed May 2, 2016.

Jeremy Thomas Dabrowiak, Craig Wendell Pendry, Christoph Matthias Pistor, "Patient Heat Exchange System with Two and Only Two Fluid Loops", related U.S. Appl. No. 14/180,719, Non-Final Office Action dated Jun. 7, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System" file history of related U.S. Appl. No. 14/180,613, filed Feb. 14, 2014.

Christoph Matthias Pistor, Jeremy Thomas Dabrowiak, Christo Pamichev, "Fluid Cassette with Polymeric Membranes and Integral Inlet and Outlet Tubes for Patient Heat Exchange System" file history of related U.S. Appl. No. 14/180,655, filed Feb. 14, 2014.

Jeremy Thomas Dabrowiak, Braig Wendell Pendry, Christop Matthias Pistor, "Patient Heat Exchange System with Two or Only Two Fluid Loops" file history of related U.S. Appl. No. 14/180,719, filed Feb. 14, 2014.

Jeremy Thomas Dabrowiak, "Heat Exchange System for Patient Temperature Control with Multiple Coolant Chambers for Multiple Heat Exchange Modalities" file history of related U.S. Appl. No. 14/175,545, filed Feb. 7, 2014.

Jeremy Thomas Dabrowiak, Eric Peterson, "Patient Heat Exchange System with Transparent Wall for Viewing Circulating Refrigerant" file history of related U.S. Appl. No. 14/276,202, filed May 13, 2014.

American Urethane Inc., "Polyurethane Properties", available Oct. 12, 2010, http://web.archive.org/web/20101012211957/http://americanurethane.com/polyurethane-properties.html.

Christoph Matthias Pistor, Jeremy Thomas Dabrowiak, Craig Wendell Pendry, Christo Pamichev, "Fluid Cassette With Polymeric Membranes and Integral Inlet and Outlet Tubes for Patient Heat Exchange System", related U.S. Appl. No. 14/180,655, Final Office dated Sep. 8, 2016.

Jeremy Thomas Dabrowiak, Craig Wendell Pendry, Christoph Matthias Pistor, "Patient Heat Exchange System with Two and Only Two Fluid Loops", related U.S. Appl. No. 14/180,719, Applicant's response to the Non-Final Office Action filed Sep. 7, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613 final office action dated Jul. 15, 2016.

Jeremy Thomas Dabrowiak, Eric Peterson, "Patient Heat Exchange System with Transparent Wall for Viewing Circulating Refrigerant", related pending U.S. Appl. No. 14/276,202 final office action dated Jul. 15, 2016.

\* cited by examiner

HEAT EXCHANGE SYSTEM FOR PATIENT TEMPERATURE CONTROL WITH EASY LOADING HIGH PERFORMANCE PERISTALTIC PUMP

FIELD OF THE INVENTION

The present application relates generally to heat exchange systems for patient temperature control with easy loading high performance peristaltic pumps.

BACKGROUND OF THE INVENTION

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 7,914,564, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

In general, in all of the intravascular and external patient temperature control solutions, the temperature of the working fluid flowing through the catheter or pad is regulated by a heat exchange console based on feedback provided by the patient's actual body temperature, typically core body temperature as may be variously measured rectally, esophageally, tympanic ear temperature, blood temperature in, e.g., the vena cava, etc. The working fluid temperature is regulated by thermally coupling the working fluid to heating and/or cooling elements in the console. In many cases, the working fluid is forced in a closed fluid circuit path (including the console and the catheter or pad) by a peristaltic pump acting on IV tubing in the fluid circuit path.

SUMMARY OF THE INVENTION

As understood herein, peristaltic pumps typically include a rotor for revolving one or more rollers against an IV tube to force fluid through the tube by peristalsis, and an arcuate raceway against which the tube is urged by the rollers. The ease by which the tube can be loaded between the rollers and raceway competes with the performance of the pump: an easier to load pump typically has lower performance, whereas a higher performance pump (with higher pumping pressure and fluid flow) usually entails more complex loading of the tube. This is because in easy to load pumps, the raceway is typically movable away from the rollers to facilitate easily placing the tube between the rollers and raceway, but higher performance pumps require longer raceways (greater than 180 degrees of arc) that are generally not movable away from the pump, complicating the task of loading the tube (which for high performance applications is relatively thick and inflexible compared to low performance tubes) between the rollers and raceway.

Accordingly, a pump has an arcuate raceway with a concave inner surface extending through an arc of at least one hundred eighty degrees (180°). The arc defines a midpoint, and a rotor feces the inner surface of the raceway and is both rotatable relative to the raceway and translationally mounted relative to the raceway between a pump position, wherein the rotor is spaced from the midpoint a first distance, and a tube load position, wherein the rotor is spaced from the midpoint a second distance greater than the first distance. A motor is coupled to the rotor to rotate the rotor. Plural rollers are arranged on the rotor to contact tubing disposed between the rotor and the raceway at least when the rotor is in the pump position. The motor is prevented from stopping at least one angular position in which at least one roller is in a predetermined location.

If desired, the concave inner surface of the raceway may extend through an arc of between one hundred eighty degrees (180°) and two hundred degrees (200°). The rollers can include at least one drive roller on the rotor. The drive roller can have a cylindrical outer surface, with the entire outer surface being configured to urge against a tube disposed between the rotor and the raceway when the rotor is in the pump position and is rotated. The drive roller has no flanges with peripheries extending beyond the cylindrical outer surface. At least one guide roller may be on the rotor and may have a cylindrical outer surface and top and bottom flanges defining respective peripheries extending beyond the cylindrical outer surface of the guide roller. With this structure, a tube disposed between the rotor and the raceway is received on the cylindrical outer surface of the guide roller between the flanges when the rotor is in the pump position and is rotated. Plural drive rollers and plural guide rollers may be provided; in some implementations, two and only two drive rollers and two and only two guide rollers are provided.

In examples, a motor mount supports the motor and rotor and a positioning mechanism is coupled to the motor mount and is manipulable by a person to move the motor mount to thereby move the rotor between the pump position and the tube load position. The motor mount can be parallel to the raceway when the rotor is in the pump position and obliquely angled relative to the raceway when the rotor is in the tube load position.

In examples discussed further below, the arc of the raceway defines opposed arc ends, and the predetermined location of the roller corresponding to the angular position at which the motor is prevented from stopping is at an arc end. To this end, a controller can be configured for controlling the motor and an angular position sensor can be configured for sensing angular position of the motor and generating a signal indicative thereof to the controller. The controller is configured to use the signal to prevent the motor from stopping at the angular position in which at least one roller is in the predetermined location.

In another aspect a method includes rotating a peristaltic pump rotor relative to a raceway to urge fluid through a tube disposed between the raceway and the rotor. The method also includes automatically preventing the rotor from stopping at one or more predetermined angular positions.

In another aspect, a pump includes a raceway, a rotor spaced from the raceway, and a motor configured to rotate the rotor to urge fluid through a tube disposed between the raceway and the rotor. A controller is configured to control the motor to automatically prevent the motor from stopping at one or more predetermined angular positions.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
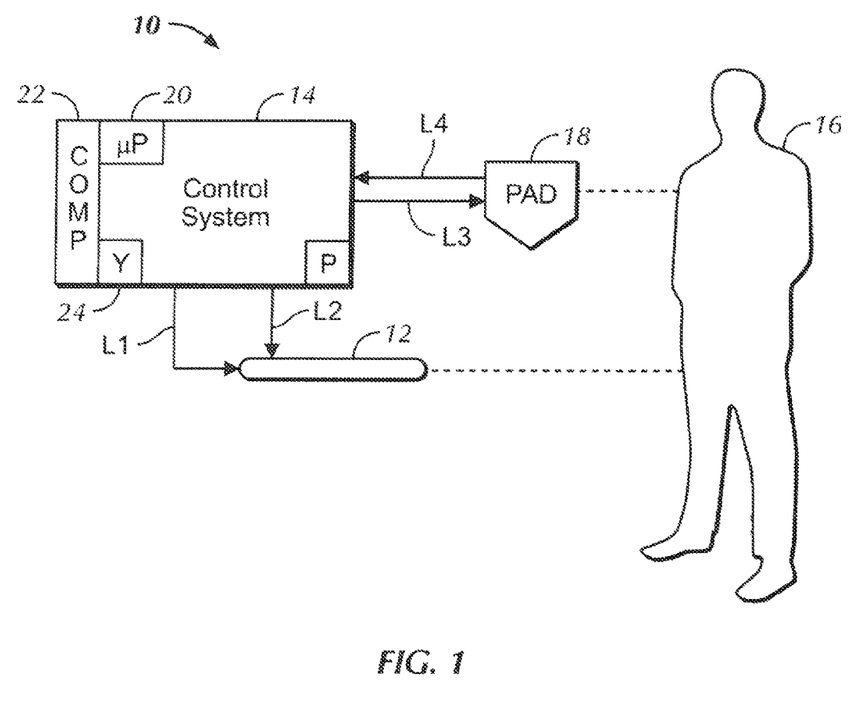
FIG. 1 is a schematic view of a non-limiting system in accordance with the present invention.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid (also referred to as "coolant") such as but not limited to saline circulates (typically under the influence of a pump "P" in the control system) in a closed loop from the control system 14, through a fluid supply line L1, through the catheter 12, and back to the system 14 through a fluid return line L2, such that no coolant enters the body. While certain preferred catheters are disclosed herein, it is to be understood that other catheters can be used in accordance with present principles, including, without limitation, any of the catheters disclosed above or in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,323,818, 6,409,747, 6,368,304, 6,338,727, 6,299,599, 6,287,326, 6,126,684, 7,211,106. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by the control system 14 to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 14 through a fluid supply line L3, and return working fluid to the system 14 through a fluid return line L4. The pump "P" may be a peristaltic pump which engages any one of the lines L1-L4, which are typically plastic IV lines, to urge working fluid through the lines through peristalsis.

The control system 14 may include one or more microprocessors 20 receiving target and patient temperatures as input and controlling, among other things, the pump "P" and a refrigerant compressor 22 with a bypass valve 24 that can be opened to permit refrigerant to bypass the compressor.

Turning now to FIGS. 2-5, an example of the pump "P" in FIG. 1 is shown and generally designated 30. The pump 30 includes a rigid, preferably metal or hard plastic raceway 32 and a rotor 34. The raceway 32 may be formed from a block of material as shown and has an inner arcuate surface 36 which may have a substantially constant radius of curvature. In some examples, the arcuate surface 36, which defines a midpoint 38 between its two ends 40, 42 (labeled in FIG. 3), can extend through an arc of at least one hundred eighty degrees (180°) and may extend through an arc of between one hundred eighty degrees (180°) and two hundred degrees (200°). In the example shown, the arcuate surface 36 extends, from one end 40 to the other end 42, through an approximately 200° arc.

As understood herein, covering more than 180° degrees of arc with the raceway provides an extra margin against internal leakage due to a pump roller not fully compressing the tubing against the raceway (a flaw colloquially known as "blowby"). Furthermore, it is possible that covering more than 180° degrees of arc allows the tubing to open gradually after being compressed by a drive roller and thereby reduce the degree of pulsatility of the flow. This in turn can reduce the amount of unwanted movement experienced by the downstream tubing and catheter when subject to pulsating flow.

Figure 2:
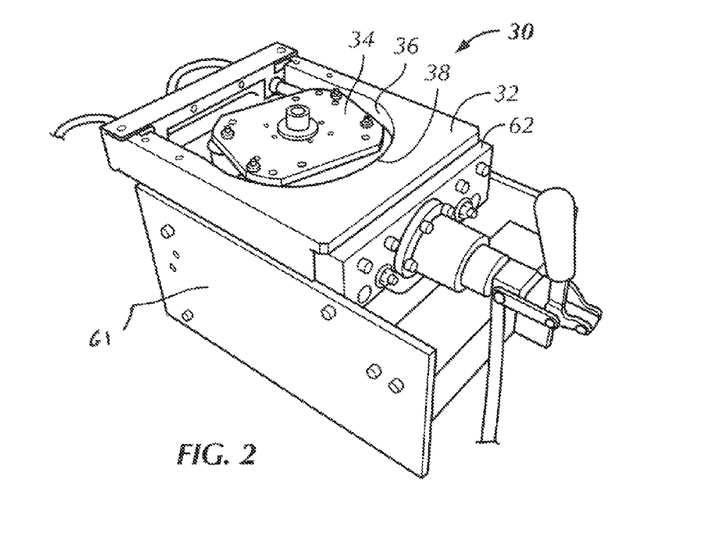
FIG. 2 is a perspective view of the pump with the rotor in the pump position.
Figure 3:
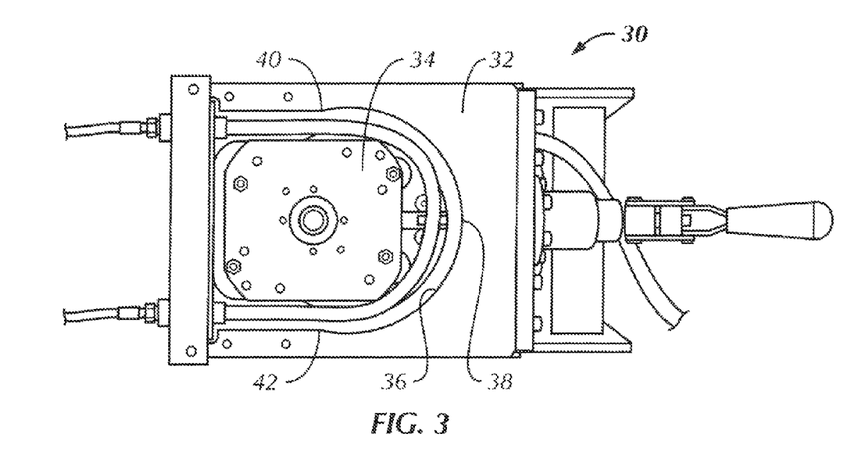
FIG. 3 is a top view of the pump with the rotor in the pump position.
Figure 4:
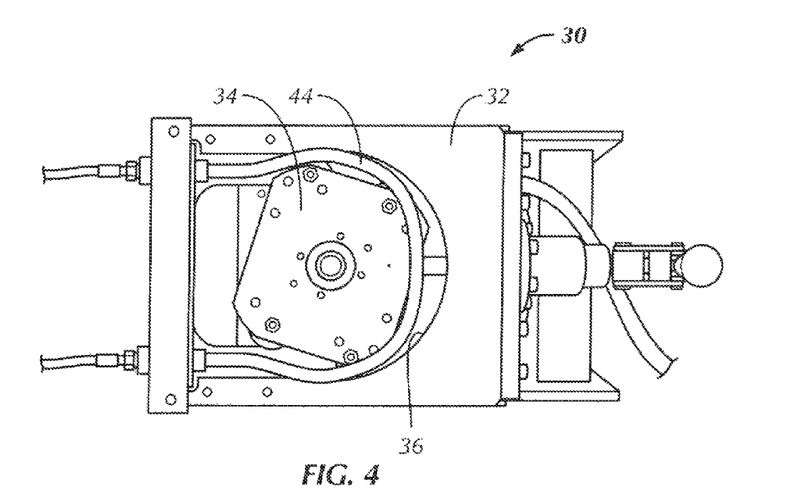
FIG. 4 is a perspective view of the pump with the rotor in the tube load position, illustrating a person manually loading the tube between the raceway and the rotor.
Figure 5:
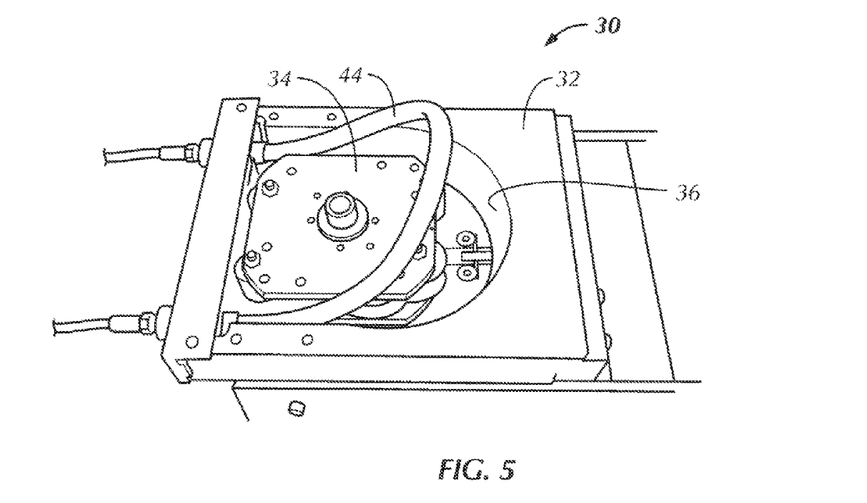
FIG. 5 is a top view of the pump with the rotor in the tube load position.

A motor, described further below, rotates the rotor 34 relative to the raceway 32. As well, the rotor 34 is movable translationally relative to the raceway 32 between a pump position (FIGS. 2, 3, 6, 7, and 9), in which the rotor 34 is spaced from the midpoint 38 of the inner surface 36 of the raceway 32 a first distance, and a tube load position (FIGS. 4, 5, and 8), in which the rotor 34 is spaced from the midpoint 38 a greater, second distance. As shown in FIGS. 2 and 3, in the pump position, rollers on the rotor 34 urge against a tube such as an IV tube that disposed between the rollers and the raceway 32. In the tube position, the rotor 34 is sufficiently spaced from the raceway 32 to permit a tube 44 to be disposed between the raceway and rotor and to be removed therefrom by hand. Example mechanisms for moving the rotor translationally are discussed further below.

Indeed and now referring to FIGS. 6-9 for example structure, mounted on the rotor 34 are at least one and preferably plural rollers to urge against the tube 44 to pump fluid through the tube. In the example shown in FIG. 6, the rotor is defined in part by a rectilinear, non-square body, and each corner of the body a roller is mounted, potentially rotatably mounted to the rotor body. In the example, at one set of opposed corners on the body, drive rollers 46 are respectively mounted (only one drive roller shown in the perspective of FIG. 6), whereas at the other set of opposed corners on the body, guide rollers 48 are respectively mounted. Thus, between the drive rollers 46 are guide rollers 48.

Figure 6:
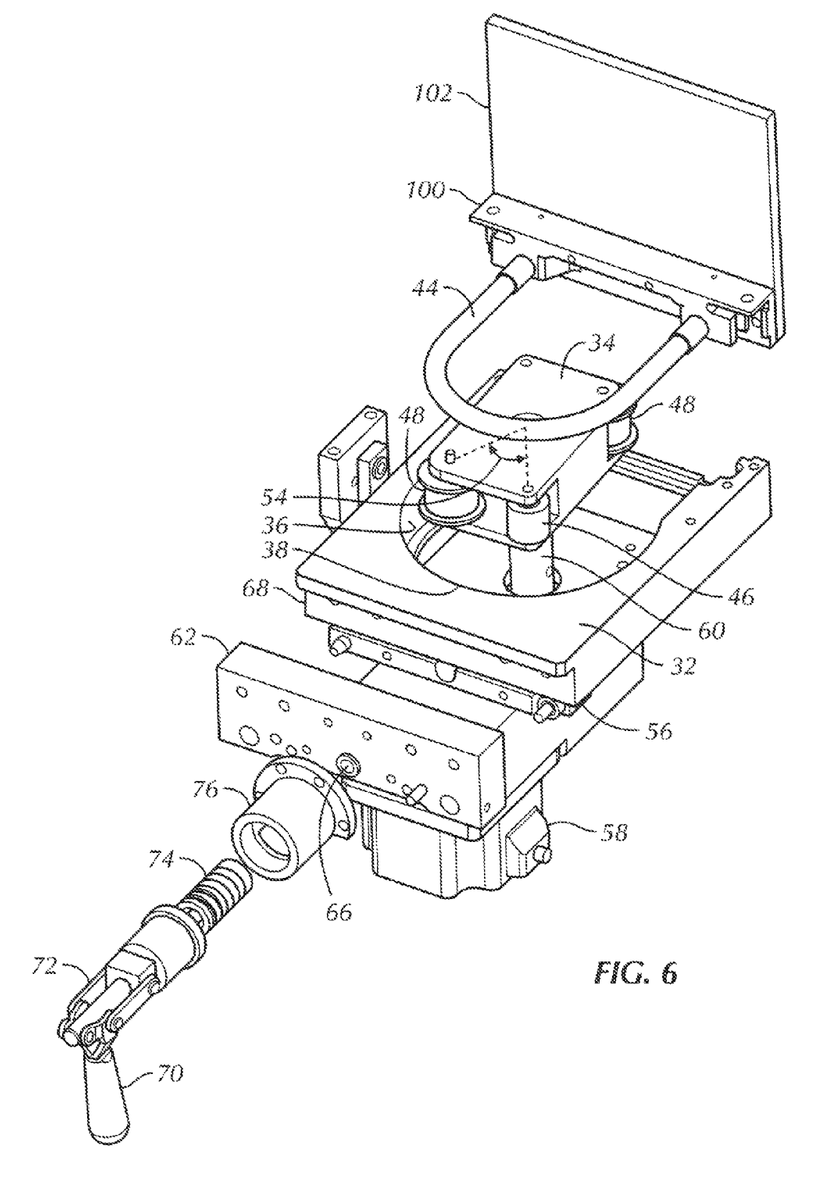
FIGS. 6 and 7 are exploded perspective views from the bottom and top, respectively, of the pump, illustrating features of an example embodiment, with portions broken away in FIG. 7.

As shown in FIG. 6, the drive roller 46 has a cylindrical outer surface, and the entire outer surface is configured to urge against the tube 44. In other words, the entire outer surface of the example drive roller is a single smooth cylinder without any flanges having peripheries extending beyond the cylindrical outer surface. In contrast, FIG. 7 best shows that the guide roller 48 also has a cylindrical outer surface but in addition includes top and bottom flanges 50, 52 defining respective peripheries extending beyond the cylindrical outer surface of the guide roller such that the tube 44 can be received on the cylindrical outer surface of the guide roller between the flanges 50, 52 when the rotor is in the pump position and is rotated. In the example shown, two and only two drive rollers 46 and two and only two guide rollers 48 are provided.

Also, in the example shown, owing to the non-square shape of the rotor 34 body, the angle 54 between the drive roller 46 and guide roller 48 at one of the ends of the rotor body, with a vertex on a point on the roller body (e.g., the midpoint), is not ninety degrees. Instead, in the example shown, the angle 54 may be, for example, fifty five degrees. The same angle obtains at the opposite end of the rotor body. However, in some embodiments the rotor body is square, in which case all rollers are separated from the adjacent rollers by ninety degrees.

A block-like motor mount 56 supports a motor 58 such as a small ac or dc motor, in some embodiments, a stepper motor or other appropriate motor type. The motor 58 is coupled to the rotor 34 by an output shaft 60, with, in some embodiments, a reduction gear train (not shown) being meshed between the motor shaft and the output shaft 60.

A positioning mechanism is coupled to the motor mount 56 and is manipulable by a person to move the motor mount 56 to thereby move the rotor 34 between the pump position and the tube load position. In a non-limiting example, referring briefly back to FIG. 2, a base 61 stationarily holds the raceway 32, and a preferably rectilinear rigid support block 62 (FIGS. 2 and 6-9) is bolted or welded to the base 61 or made integrally therewith. A push rod 64 (FIGS. 7-9) extends through a hole 66 in the support block 62 to contact and/or be engaged with the motor mount 56 and/or with a motor plate 68 coupled to the motor mount 56. A handle 70 is coupled at a hinge mechanism 72 to the push rod 64. The handle can be moved by hand to a substantially perpendicular orientation relative to the push rod 64 (FIGS. 6 and 9) to pull the push rod and thus to move the motor mount 56 (and hence rotor 34) toward the inner surface of the raceway 32, thereby moving the rotor 34 to the pump position. The handle can also be moved by hand down from the perpendicular orientation to the non-perpendicular orientation shown in FIGS. 7 and 8. This pushes the push rod 64 and thus moves the motor mount 56/rotor 34 away from the pump position to the tube load position. One or more radial bearings 74, 76 may be provided as appropriate to radially support elements of the positioning mechanism.

Figure 7:
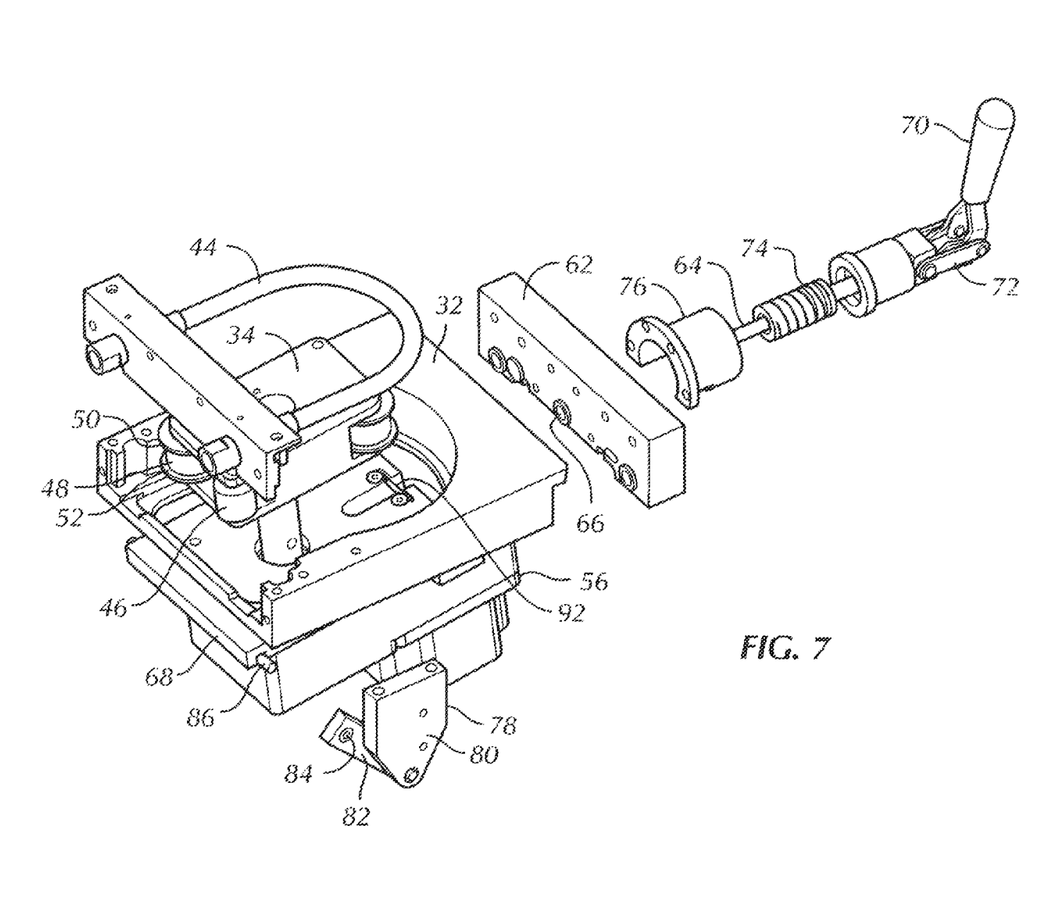

Also and focusing on FIG. 7, to support the motor mount 56 and attendant elements that move with it, two side brackets 78 may be provided on respective sides of the raceway 32 (only one bracket 78 shown in FIG. 7). A vertical flange 80 of the side bracket 78 may be affixed to the raceway 32, e.g., by threaded fasteners or welding, and a swing arm 82 pivotably coupled to the vertical flange 80 and rotatably coupled to the motor mount 56 or other component that moves with the motor mount. In the example shown in FIG. 7, a hole 84 is formed in the swing arm 82 and rotatably engages a pin 86 that is attached to and that extends radially away from the motor plate 68. Recall that the motor mount 56, motor plate 68, and rotor 34 move translationally together as unit.

Figure 8:
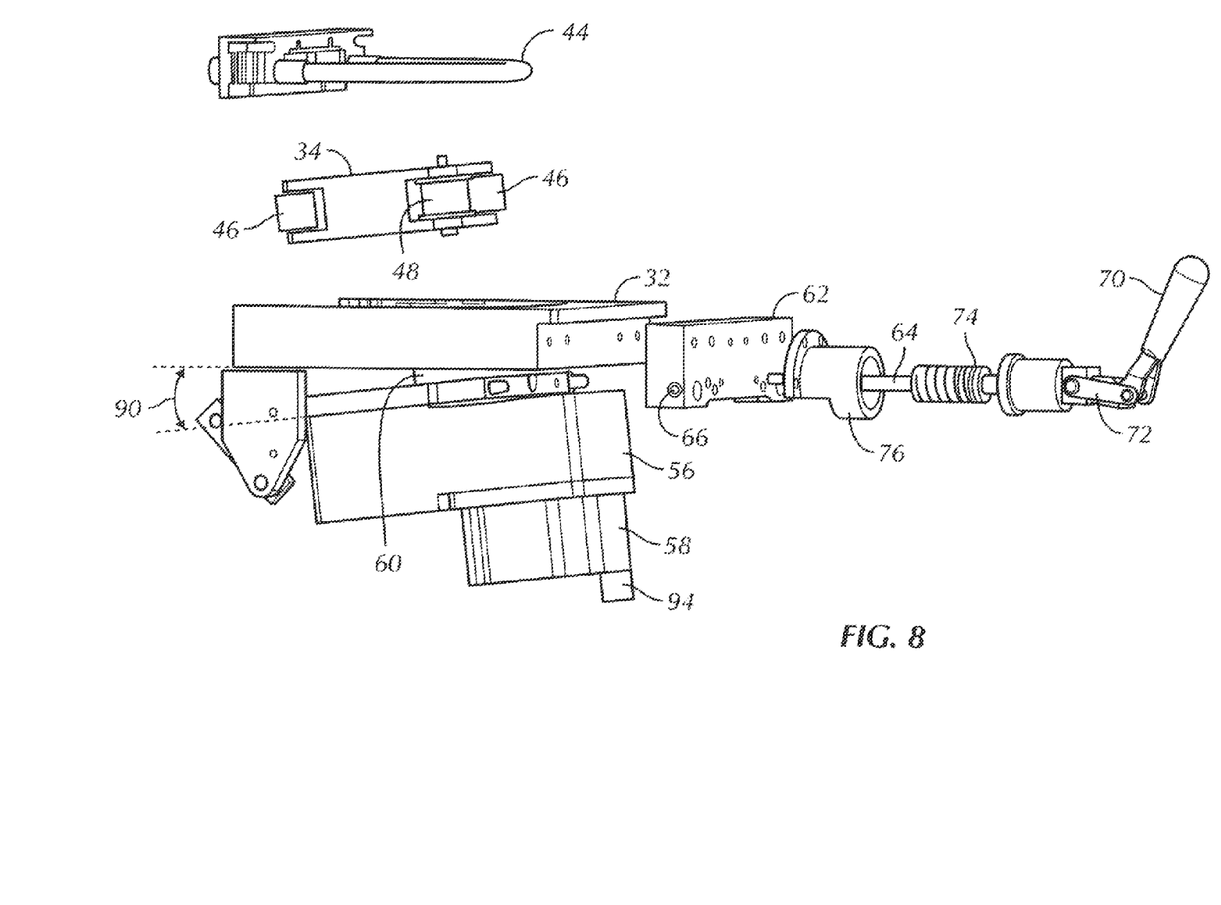
FIGS. 8 and 9 are exploded side views respectively showing the relationship between the motor mount and the raceway in the tube load and pump positions of the rotor, with some portions broken away.
Figure 9:
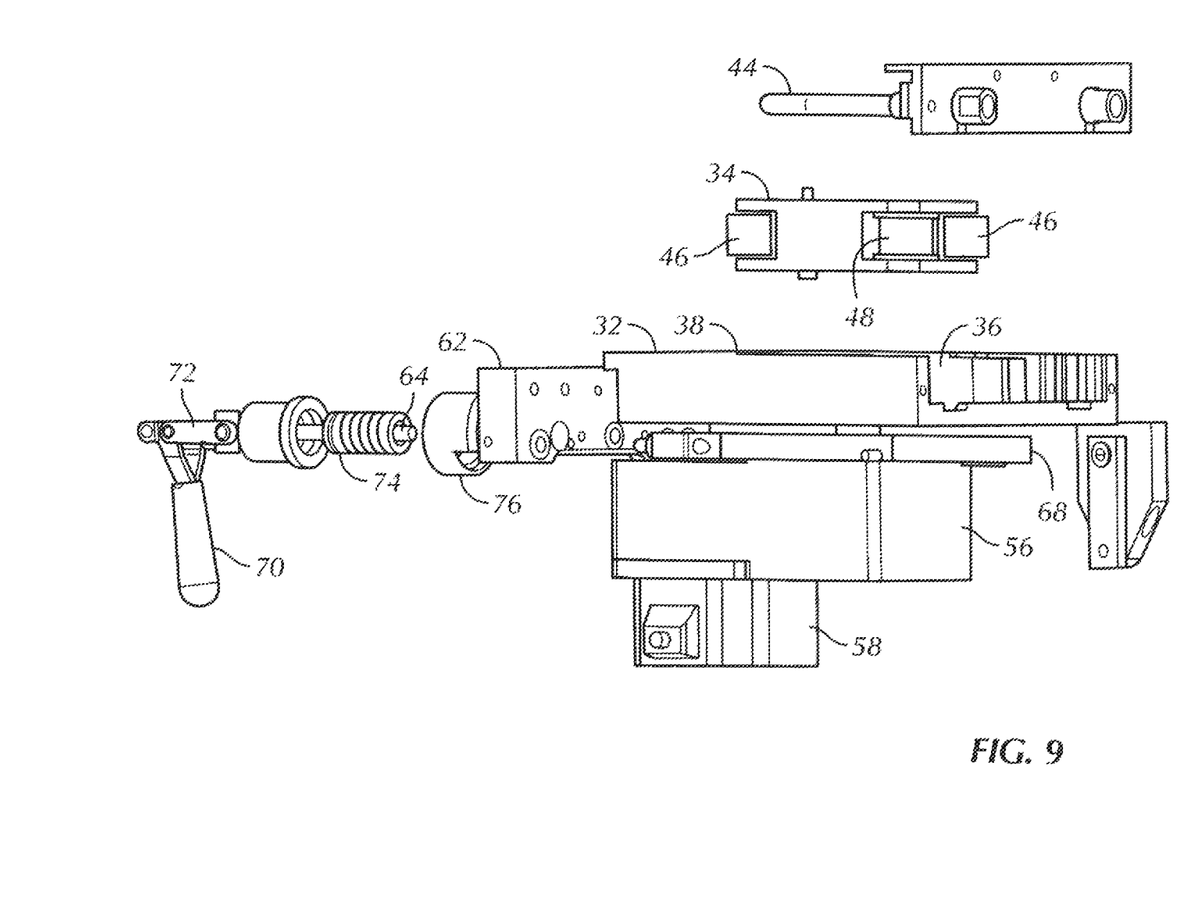

Owing to the example positioning mechanism described above, as best shown in FIG. 9 the motor mount 56 (with motor plate 68) is parallel to the raceway 32 when the rotor 34 is in the pump position. In contrast, as best shown in FIG. 8 the motor mount 56 (with motor plate 68) is obliquely angled relative to the raceway 32 when the rotor 34 is in the tube load position. That is, an oblique angle 90 is established between, for example, the plane of the motor plate 68 and the plane defined by the bottom surface of the raceway 32 when the rotor 34 is in the tube load position. To further facilitate motion of the positioning mechanism when the handle 70 is moved, a hinge pin 92 (FIG. 7) may be provided as part of the coupling between the push rod 64 and motor mount 56/motor plate 68.

Thus, the rotor 34 can move linearly relative to raceway 32. In the example shown, linear bearings are used, it being understood that equivalency a multi-bar linkage between the rotor and raceway can be used for pseudo-linear motion. In any case, in the tube position the rotor is a sufficient distance (typically an inch or more) so that the tube 44 can be inserted freely between the rotor and raceway by a person. Then, when the rotor is moved to the pump position, at least the drive rollers 46 urge into the tube 44 sufficiently to stretch the tube 44 by an elongation of at least 3% and typically 3-15%. This elongation advantageously ensures that slack does not build up in the tubing as it wears and stretches during use. As understood herein, such slack can lead to kinking of the tubing or excessive wear.

FIG. 8 is used to schematically show that at least one angular position sensor 94 can be provided on the motor 58. Without limitation, the angular position sensor may be a Hall effect sensor, or a dc stepper motor revolution counter, or a potentiometer type sensor. The sensor 94 generates an output representative of the angular position of the motor. The sensor 94 may be coupled to the motor shaft or the output shaft 60 or other part of the rotating mechanism in the pump.

In any case, the processor 20 shown in FIG. 1 can control the motor 58 and can receive the signal from the sensor 94. Using the signal from the sensor 94, the processor 20 can prevent the motor 58 from stopping at an angular position corresponding to at least one roller 46/48 being in a predetermined angular location relative to the raceway 32. In an example, the predetermined location of the roller corresponding to the angular position at which the motor is prevented from stopping is at an arc end 40 or 42 of the raceway 32. This ensures that, particularly when a raceway arc of >180 degrees is used, the rollers will not be in the 12 o'clock and 6 o'clock positions (i.e., adjacent to the ends of the arc), which would interfere with the raceway even when the rotor is in the tube load position and thereby complicate tube loading and unloading.

Thus, the position sensor 94 can be coupled to the motor shaft to indicate critical angular positions to avoid stopping the motor at. The processor 20 can control the motor so that it will not stop on these critical positions. Alternately, the signal from the one or more sensors 94 can be used to indicate non-critical positions, with the processor 20 controlling the motor so it will always stop on these non-critical angular positions. Yet again, a mechanical may be used to ensure that the motor/rotor does not stop in critical positions.

Completing the description, the tube 44 may be configured as a loop as best shown in FIG. 6, with the ends of the loop engaged with a manifold 100 in fluid communication with the interior of the manifold 10. In turn, the interior of the manifold 100 may communicate with a cassette 102 such as the cassette shown and described in U.S. patent application Ser. No. 14/180,655, filed Feb. 24, 2014 and incorporated herein by reference. Such a cassette can be engaged with structure in the control system 14 to exchange heat with working fluid flowing through the cassette 102 and tube 44 and being circulated by the pump shown and described herein to and from a heat exchange member such as the catheter 12/pad 18.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

While the particular HEAT EXCHANGE SYSTEM FOR PATIENT TEMPERATURE CONTROL WITH EASY LOADING HIGH PERFORMANCE PERISTALTIC PUMP is herein shown and described in detail, the scope of the present invention is to be limited by nothing other than the appended claims.

What is claimed is:

1. Pump, comprising:
    an arcuate raceway having a concave inner surface extending through an arc of at least one hundred eighty degrees, the arc defining a midpoint;
    a rotor facing the inner surface of the raceway, the rotor being rotatable relative to the raceway, the rotor being translationally mounted relative to the raceway between a pump position, wherein the rotor is spaced from the midpoint a first distance, and a tube load position, wherein the rotor is spaced from the midpoint a second distance greater than the first distance;
    a motor coupled to the rotor to rotate the rotor;
    plural rollers arranged on the rotor to contact tubing disposed between the rotor and the raceway at least when the rotor is in the pump position;
    a motor mount supporting the motor and rotor; and
    a positioning mechanism coupled to the motor mount and including a handle manipulable by a person to move the motor mount to thereby move the rotor between the pump position and the tube load position, the positioning mechanism including a rod coupled to the motor mount, the handle being coupled to the rod such that the handle is movable to a first orientation to move the rod and move the motor mount and hence the rotor toward the inner surface of the raceway, moving the rotor to the pump position, the handle being movable to a second orientation to move the rod and move the rotor toward the tube load position.

2. The pump of claim 1, wherein the concave inner surface of the raceway extends through an arc of between one hundred eighty degrees and two hundred degrees.

3. The pump of claim 1, wherein the rollers comprise:
    at least one drive roller on the rotor, the drive roller having a cylindrical outer surface, the entire outer surface being configured to urge against a tube disposed between the rotor and the raceway when the rotor is in the pump position and is rotated, the drive roller having no flanges with peripheries extending beyond the cylindrical outer surface; and
    at least one guide roller on the rotor, the guide roller having a cylindrical outer surface and top and bottom flanges defining respective peripheries extending beyond the cylindrical outer surface of the guide roller such that a tube disposed between the rotor and the raceway is received on the cylindrical outer surface of the guide roller between the flanges when the rotor is in the pump position and is rotated.

4. The pump of claim 3, comprising plural drive rollers and plural guide rollers.

5. The pump of claim 3, comprising two and only two drive rollers and two and only two guide rollers.

6. The pump of claim 1, wherein the motor mount is parallel to the raceway when the rotor is in the pump position, the motor mount being obliquely angled relative to the raceway when the rotor is in the tube load position.

7. The pump of claim 1, wherein the motor is prevented from stopping at at least one angular position in which at least one roller is in a predetermined location, wherein the arc defines opposed arc ends, and the predetermined location of the roller corresponding to the angular position at which the motor is prevented from stopping is at an arc end.

8. The pump of claim 1, comprising a controller configured for controlling the motor and an angular position sensor configured for sensing angular position of the motor and generating a signal indicative thereof to the controller, the controller configured to use the signal to prevent the motor from stopping at an angular position in which at least one roller is in a predetermined location.

* * * * *